(12) United States Patent
Kobayashi

(10) Patent No.: US 10,271,921 B2
(45) Date of Patent: Apr. 30, 2019

(54) MEDICAL OBSERVATION APPARATUS AND MEDICAL OBSERVATION SYSTEM

(71) Applicant: Sony Olympus Medical Solutions Inc., Tokyo (JP)

(72) Inventor: Motoaki Kobayashi, Tokyo (JP)

(73) Assignee: Sony Olympus Medical Solutions Inc., Tokyo (JP)

(*) Notice: Subject to any disclaimer, the term of this patent is extended or adjusted under 35 U.S.C. 154(b) by 0 days.

(21) Appl. No.: 15/745,906

(22) PCT Filed: Jul. 11, 2016

(86) PCT No.: PCT/JP2016/070467
§ 371 (c)(1),
(2) Date: Jan. 18, 2018

(87) PCT Pub. No.: WO2017/029906
PCT Pub. Date: Feb. 23, 2017

(65) Prior Publication Data
US 2018/0200017 A1    Jul. 19, 2018

(30) Foreign Application Priority Data
Aug. 20, 2015 (JP) .................. 2015-163065

(51) Int. Cl.
*A61B 90/00* (2016.01)
*A61B 90/25* (2016.01)
(Continued)

(52) U.S. Cl.
CPC .......... *A61B 90/25* (2016.02); *G02B 21/0012* (2013.01); *G02B 21/24* (2013.01);
(Continued)

(58) Field of Classification Search
CPC ......... A61B 90/20; A61B 90/25; A61B 90/37; A61B 2090/373; A61B 1/00147–00147;
(Continued)

(56) References Cited

U.S. PATENT DOCUMENTS 4,793,203 A     12/1988  Staggl et al.
2004/0138650 A1  7/2004  Nakamura
(Continued)

FOREIGN PATENT DOCUMENTS

EP  0 873 826 A2  10/1998
EP  1 352 721 A1  10/2003
(Continued)

OTHER PUBLICATIONS

International Search Report dated Sep. 13, 2016 in PCT/JP2016/070467 filed Jul. 11, 2016.
(Continued)

*Primary Examiner* — Stephone B Allen
*Assistant Examiner* — Adam W Booher
(74) *Attorney, Agent, or Firm* — Oblon, McClelland, Maier & Neustadt, L.L.P.

(57) ABSTRACT

A medical observation apparatus according to the present invention includes a microscope unit, a support unit that movably supports the microscope unit and that includes a plurality of arm portions and a plurality of joint portions, each of which holds the arm portions rotatably about a predetermined axis, and a cable connected to the microscope unit and inserted through an interior of the support unit, wherein at least one of the joint portions includes a twisting joint portion that rotates a rotation-target arm portion about an axis parallel to a central axis of the rotation-target arm portion, and the twisting joint portion includes a rotational-shaft portion, a rotational portion that holds the rotation-target arm portion, fixes the cable at a position offset from
(Continued)

the central axis of the rotational-shaft portion, and is rotatable about the central axis, and an extending portion that extends from the rotational-shaft portion.

20 Claims, 9 Drawing Sheets

(51) Int. Cl.
  *G02B 21/00* (2006.01)
  *G02B 21/24* (2006.01)
  *G02B 21/32* (2006.01)
  *G02B 21/36* (2006.01)
(52) U.S. Cl.
  CPC ........ *G02B 21/32* (2013.01); *A61B 2090/373* (2016.02); *G02B 21/368* (2013.01)
(58) Field of Classification Search
  CPC ... A61B 1/008; A61B 2034/305; A61B 90/50; A61B 90/53; A61B 90/57; A61B 2090/5025; A61B 2090/504; A61B 2090/506; A61B 2090/508; G02B 21/0012; G02B 21/24; G02B 21/32; G02B 21/36; G02B 21/362; G02B 21/364; G02B 21/368; G02B 7/001; B25J 17/00–17/0291; B25J 19/021; B25J 19/023; B25J 19/025; B25J 9/06; B25J 18/04; B25J 18/06
  See application file for complete search history.

(56) References Cited

U.S. PATENT DOCUMENTS

2005/0057800 A1 3/2005 Obrebski et al.
2017/0307836 A1* 10/2017 Iwasaki ................ B25J 19/0029

FOREIGN PATENT DOCUMENTS

| EP | 2 829 369 A2 | 1/2015 |
|---|---|---|
| JP | 63-68380 A | 3/1988 |
| JP | 7-56003 Y2 | 12/1995 |
| JP | 10-33554 A | 2/1998 |
| JP | 2000-210302 A | 8/2000 |
| JP | 2002-370190 A | 12/2002 |
| JP | 2004-208845 A | 7/2004 |
| WO | 2015/046081 A1 | 4/2015 |

OTHER PUBLICATIONS

Written Opinion dated Sep. 13, 2016 in PCT/JP2016/070467 filed Jul. 11, 2016.
Extended European Search Report dated Feb. 19, 2019 in European Application No. 16836898.3, filed Jul. 11, 2016 6 pp.

* cited by examiner

MEDICAL OBSERVATION APPARATUS AND MEDICAL OBSERVATION SYSTEM

TECHNICAL FIELD

The present invention relates to a medical observation apparatus and a medical observation system.

BACKGROUND ART

An optical microscope system has been conventionally known as a medical observation system to observe a microscopic part in the brain, heart, and the like of a patient that is an observation target at the time of performing medical surgery on the microscopic part. The optical microscope system includes an optical magnification system that magnifies the microscopic part (for example, see Patent Literatures 1 to 3).

The microscope system disclosed in Patent Literatures 1 to 3 includes a microscope unit in which an imaging unit is incorporated, and a support unit that includes a plurality of arms provided to be rotatable with respect to each other, and that supports the microscope unit. By rotating each of the arms, the microscope system can move or tilt the microscope unit three-dimensionally to a desired position.

Further, in the microscope system disclosed in Patent Literatures 1 to 3, a cable is inserted through the interior of the arms. The cable includes a plurality of transmission lines connecting the imaging unit and a control unit that controls the operation and the like of the imaging unit, in order to transmit a control signal from the control unit to the imaging unit, and transmit a signal generated from an image captured by the imaging unit to the control unit.

CITATION LIST

Patent Literatures

Patent Literature 1: Japanese Utility Model Publication No. 7-56003
Patent Literature 2: Japanese Laid-open Patent Publication No. 10-33554
Patent Literature 3: Japanese Laid-open Patent Publication No. 2000-210302

DISCLOSURE OF INVENTION

Technical Problem

Meanwhile, the microscope system disclosed in Patent Literatures 1 to 3 does not take into account a load to be applied to the cable due to rotation of the arm. Particularly, when the arm is rotated in a direction in which the cable is twisted, a twisting load is applied to the cable, which may damage the cable. Thus, a technique to provide durability against rotation of the arm has been required.

The present invention has been made in view of the above, and an object of the present invention is to provide a medical observation apparatus and a medical observation system that have durability against rotation of an arm.

Solution to Problem

In order to solve the above problem and to achieve the object, a medical observation apparatus according to the present invention includes: a microscope unit that outputs a signal of a captured image of an observation target; a support unit that movably supports the microscope unit and that includes a plurality of arm portions and a plurality of joint portions, each of which holds the arm portions rotatably about a predetermined axis; and one or a plurality of cables connected to the microscope unit and inserted through an interior of the support unit, wherein at least one of the joint portions includes a twisting joint portion that rotates a rotation-target arm portion about an axis parallel to a central axis of the rotation-target arm portion, and the twisting joint portion includes a rotational-shaft portion that extends in parallel to the central axis of the rotation-target arm portion, a rotational portion that holds the rotation-target arm portion, fixes the cable at a position offset from a central axis of the rotational-shaft portion, and is rotatable about the central axis, and an extending portion that extends from the rotational-shaft portion and fixes the cable at a position where the central axis of the rotational-shaft portion passes through the cable.

In the medical observation apparatus according to the present invention, the extending portion includes a fixed portion fixed to the rotational-shaft portion, and a connecting portion having a plate shape that fixes the cable thereto and is connected with the fixed portion.

In the medical observation apparatus according to the present invention, the rotational portion has a cylindrical shape and is located on an outer peripheral side of the rotational-shaft portion, and a plate width of the connecting portion on a main surface is smaller than an outer peripheral diameter of the rotational portion.

In the medical observation apparatus according to the present invention, a relation $2 \times R_1 \leq D_1$ is satisfied, where $R1$ represents a diameter of the cable, and $D_1$ represents a distance between the central axis of the rotational-shaft portion and a center of the cable.

In the medical observation apparatus according to the present invention, a fixing position of the cable in the rotational portion, and a fixing position of the cable in the extending portion are located respectively at one end and the other end of the twisting joint portion in a direction of the central axis of the rotational-shaft portion.

In the medical observation apparatus according to the present invention, at least one of the cables exists on a plane passing through the central axis of the rotational-shaft portion in a state in which the rotational portion and the extending portion are not twisted.

In the medical observation apparatus according to the present invention, in a state in which the rotational portion and the extending portion are not twisted, a plane passing through at least one of the cables and passing through the central axis of the rotational-shaft portion is a plane passing through substantially a center within a range where the cable is rotatable when the rotational portion rotates about the central axis.

A medical observation system according to the present invention includes: the medical observation apparatus according to the above invention; and a display device that displays an image corresponding to image data generated by the medical observation apparatus.

Advantageous Effects of Invention

According to the present invention, an effect is brought about, according to which a medical observation apparatus and a medical observation system that have durability against rotation of an arm can be realized.

BEST MODE FOR CARRYING OUT THE INVENTION

A mode for carrying out the present invention (hereinafter, "embodiment") will be described below with reference to the accompanying drawings. The present invention is not limited to the embodiment. Further, in the descriptions of the drawings, like parts are denoted by like reference signs. The diagrams are merely schematic, and may include a section where the dimensional relation or ratio between components differs between the drawings.

Embodiment

Figure 1:
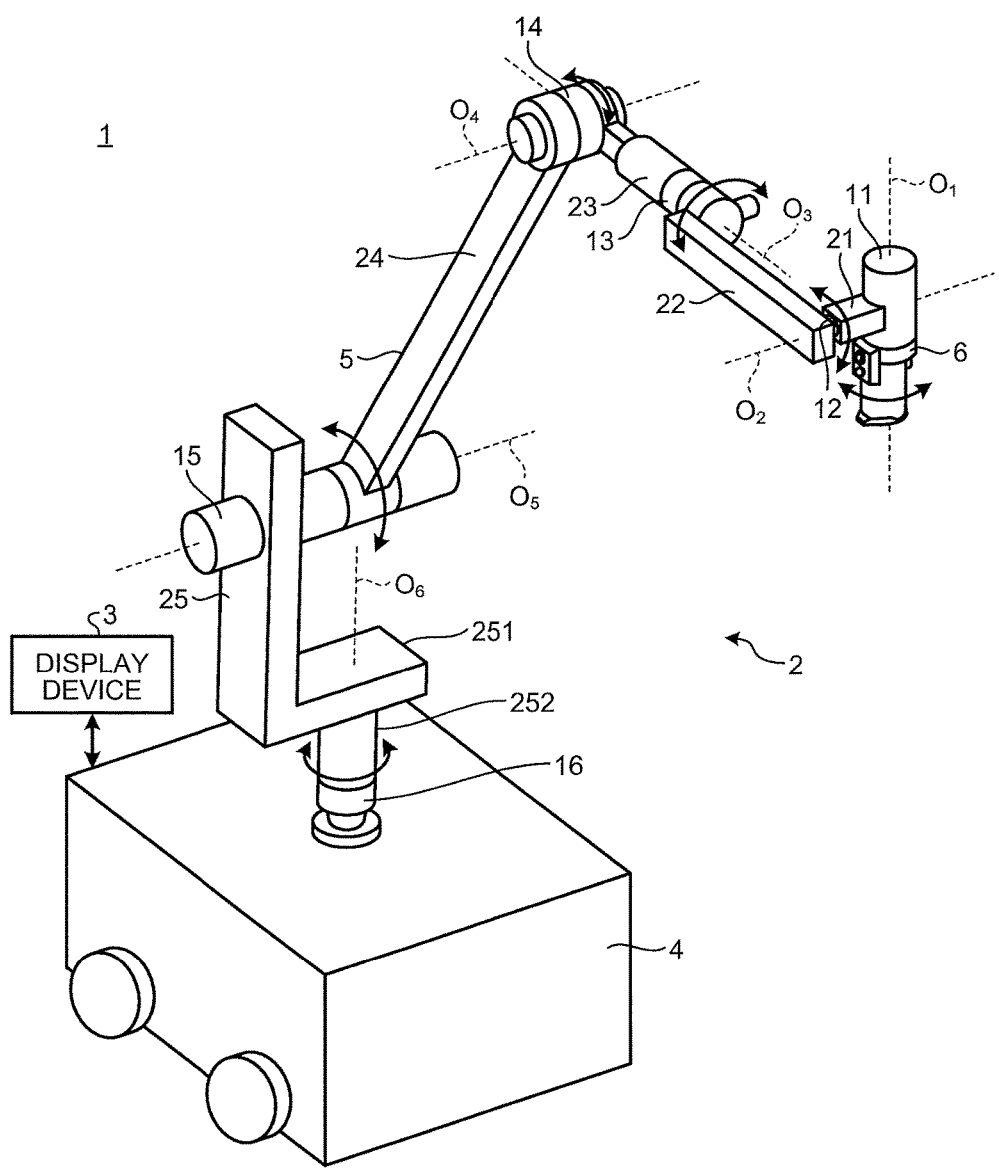
FIG. 1 is a perspective view illustrating an external appearance configuration of a medical observation system according to an embodiment of the present invention.

FIG. 1 is a perspective view illustrating an external appearance configuration of a medical observation system according to an embodiment of the present invention. A medical observation system 1 illustrated in FIG. 1 includes a medical observation apparatus (hereinafter, "observation apparatus") 2 that functions as a microscope that magnifies and images a microscopic structure of an observation target, and a display device 3 that displays an image corresponding to image data generated by the observation apparatus 2.

The observation apparatus 2 includes a base unit 4 that constitutes a base of the observation apparatus 2 and is movable on the floor, a support unit 5 that is supported by the base unit 4, and a microscope unit 6 with a columnar shape that is provided at a distal end of the support unit 5 and that magnifies and images a microscopic part of the observation target. In the base unit 4, a control unit and a light source unit are provided. The control unit generates image data on the basis of a signal of an image captured by the microscope unit 6 and integrally controls the operation of the medical observation system 1. The light source unit emits illumination light to illuminate the observation target. In the observation apparatus 2, for example, a cable group is provided to stretch from the base unit 4 to the microscope unit 6. The cable group includes a transmission cable including a signal line through which a signal is transmitted between the control unit and the microscope unit 6, and a light guide cable through which illumination light is guided from the light source unit to the microscope unit 6. The cable group is provided along the support unit 5.

The support unit 5 includes a first joint portion 11, a first arm portion 21, a second joint portion 12, a second arm portion 22, a third joint portion 13, a third arm portion 23, a fourth joint portion 14, a fourth arm portion 24, a fifth joint portion 15, a fifth arm portion 25, and a sixth joint portion 16.

The support unit 5 includes four sets of two arm portions with a joint portion connecting one (on the distal-end side) of the two arm portions rotatably to the other (on the proximal-end side). Specifically, these four sets are (the first arm portion 21, the second joint portion 12, and the second arm portion 22), (the second arm portion 22, the third joint portion 13, and the third arm portion 23), (the third arm portion 23, the fourth joint portion 14, and the fourth arm portion 24), and (the fourth arm portion 24, the fifth joint portion 15, and the fifth arm portion 25). Hereinafter, one side continuous to the base unit 4 is referred to as "proximal-end side", while the other side continuous to the microscope unit 6 is referred to as "distal-end side".

The first joint portion 11 holds on its distal-end side the microscope unit 6 rotatably, while being held on its proximal-end side by the first arm portion 21 in a fixed state at a distal-end portion of the first arm portion 21. The first joint portion 11 has a cylindrical shape and holds the microscope unit 6 rotatably about a first axis $O_1$ that is the central axis of the first joint portion 11 in its height direction. The first arm portion 21 has a shape extending from a lateral surface of the first joint portion 11 in a direction perpendicular to the first axis $O_1$.

The second joint portion 12 holds on its distal-end side the first arm portion 21 rotatably, while being held on its proximal-end side by the second arm portion 22 in a fixed state at a distal-end portion of the second arm portion 22. The second joint portion 12 has a cylindrical shape and holds the first arm portion 21 rotatably about a second axis $O_2$ that is the central axis of the second joint portion 12 in its height direction and perpendicular to the first axis $O_1$. The second arm portion 22 has a substantial L-shape, and connects to the second joint portion 12 at one end portion of the L-shape (the end portion in a longitudinal line section).

The third joint portion 13 holds on its distal-end side the other end portion of the L-shape (the end portion in a transverse line section) of the second arm portion 22 rotatably. Simultaneously, the third joint portion 13 is held on its proximal-end side by the third arm portion 23 in a fixed state at a distal-end portion of the third arm portion 23. The third joint portion 13 has a cylindrical shape and holds the second arm portion 22 rotatably about a third axis $O_3$ that is the central axis of the third joint portion 13 in its height direction, perpendicular to the second axis $O_2$, and parallel to the direction in which the second arm portion 22 extends. The third arm portion 23 has a cylindrical shape on its distal-end side. On the proximal-end side thereof, a hole that passes therethrough is formed in a direction perpendicular to the height direction of the distal-end side cylinder. The third joint portion 13 is held rotatably by the fourth joint portion 14 through this hole. The third joint portion 13 is described later in detail.

The fourth joint portion 14 holds on its distal-end side the third arm portion 23 rotatably, while being held on its proximal-end side by the fourth arm portion 24 in a fixed state at the fourth arm portion 24. The fourth joint portion 14 has a cylindrical shape and holds the third arm portion 23 rotatably about a fourth axis $O_4$ that is the central axis of the fourth joint portion 14 in its height direction and perpendicular to the third axis $O_3$.

The fifth joint portion 15 holds on its distal-end side the fourth arm portion 24 rotatably, while being fixedly attached on its proximal-end side to the fifth arm portion 25. The fifth joint portion 15 has a cylindrical shape and holds the fourth arm portion 24 rotatably about a fifth axis $O_5$ that is the central axis of the fifth joint portion 15 in its height direction and parallel to the fourth axis $O_4$. The fifth arm portion 25 is constituted by a bent portion 251 that is bent to have an L-shape, and a bar-shaped portion 252 that extends downward from a bottom surface of the bent portion 251 in a bar shape. The fifth joint portion 15 is attached on its proximal-end side to an end portion of the bent portion 251, which is opposite to the portion from which the bar-shaped portion 252 extends.

The sixth joint portion 16 holds on its distal-end side the fifth arm portion 25 rotatably, while being fixedly attached on its proximal-end side to a top surface of the base unit 4. The sixth joint portion 16 has a cylindrical shape and holds the fifth arm portion 25 rotatably about a sixth axis $O_6$ that is the central axis of the sixth joint portion 16 in its height direction and perpendicular to the fifth axis $O_5$. The proximal-end portion of the bar-shaped portion 252 of the fifth arm portion 25 is attached on the distal-end side of the sixth joint portion 16.

The support unit 5 having the configuration as described above achieves motion of the microscope unit 6 with six different degrees of freedom in total, including three different degrees of freedom in translational motion, and three different degrees of freedom in rotational motion. The cables described above are inserted through the interior of the first joint portion 11 to the sixth joint portion 16 and the first arm portion 21 to the fifth arm portion 25, so as to connect the base unit 4 and the microscope unit 6.

Each of the first joint portion 11 to the sixth joint portion 16 includes an electromagnetic brake that individually prohibits the microscope unit 6 and the first arm portion 21 to the fifth arm portion 25 from rotating. Each electromagnetic brake is released in a state in which an operation switch, described later, provided in the microscope unit 6 is depressed, and then individually allows the microscope unit 6 and the first arm portion 21 to the fifth arm portion 25 to rotate. An air brake may be adopted instead of the electromagnetic brake.

The microscope unit 6 has a cylindrical shape, and is provided therein with an imaging unit that magnifies and captures an image of the observation target. The microscope unit 6 is further provided with an operation switch that receives an input operation to release the electromagnetic brakes in the first joint portion 11 to the sixth joint portion 16, and allow each of the joint portions to rotate, and an operation lever capable of changing magnification factors and the focal distance to the observation target in the imaging unit. The optical axis of the imaging unit corresponds with, for example, the first axis $O_1$.

The imaging unit images the observation target and outputs a signal of the image under control of the control unit. The imaging unit is configured by using an imaging element such as a Charge Coupled Device (CCD), a Complementary Metal Oxide Semiconductor (CMOS), or the like that receives an optical image of the observation target and converts the image to an electric signal.

Figure 2:
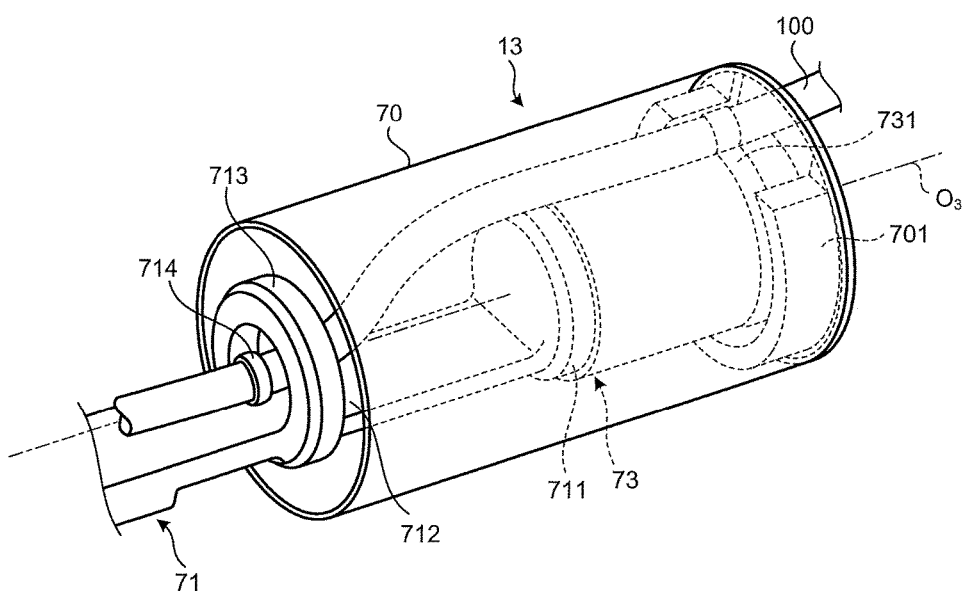
FIG. 2 is a perspective view illustrating a configuration of relevant parts of the medical observation system according to the embodiment of the present invention.
Figure 3:
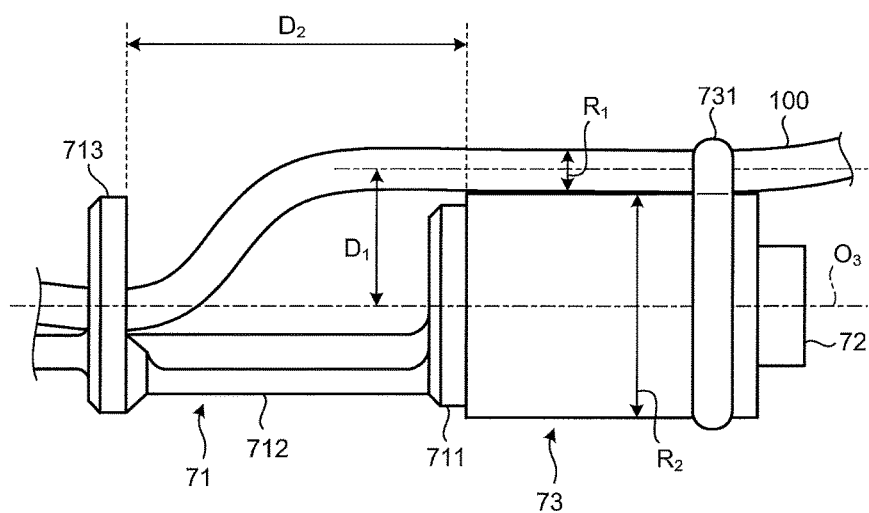
FIG. 3 is a side view illustrating a configuration of relevant parts of the medical observation system according to the embodiment of the present invention.
Figure 4:
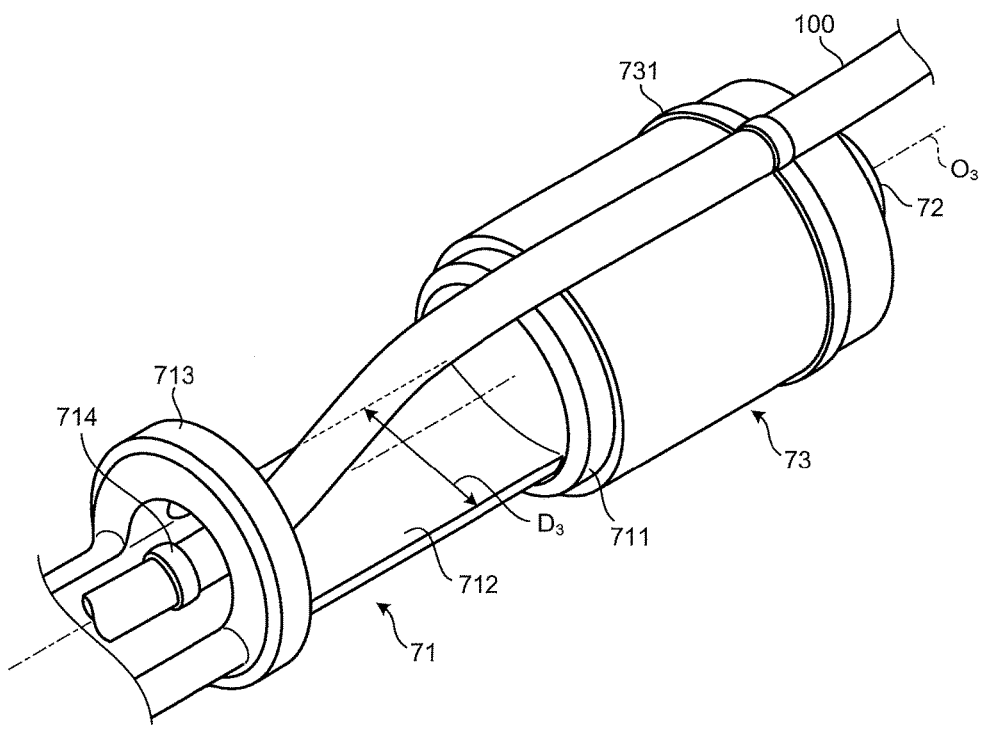
FIG. 4 is a perspective view illustrating a configuration of relevant parts of the medical observation system according to the embodiment of the present invention.

FIG. 2 is a perspective view illustrating a configuration of relevant parts of the medical observation system according to the embodiment of the present invention, in which a configuration of relevant parts of the third joint portion 13 is illustrated. FIG. 3 is a side view illustrating a configuration of relevant parts of the medical observation system according to the embodiment of the present invention, in which a cover 70 described later is removed from the configuration illustrated in FIG. 2. FIG. 4 is a perspective view illustrating a configuration of relevant parts of the medical observation system according to the embodiment of the present invention, in which the cover 70 described later is removed from the configuration illustrated in FIG. 2. FIG. 2 to FIG. 4 illustrate only a cable 100 with a largest cable diameter (for example, a light guide cable) in the cable group inserted through the support unit 5. In the present embodiment, the cable 100 is described as being positioned on the outermost periphery of the cable group. The cable 100 may be a transmission cable that constitutes the outermost periphery of the cable group in accordance with its thickness or the like. The cable 100 may be a cable that passes through the outermost periphery of the cable group in which a light guide cable and a transmission cable are located and exposed to be the outermost periphery.

The third joint portion 13 functions as a twisting joint portion that allows the second arm portion 22 to rotate about an axis parallel to the central axis of the second arm portion 22. FIG. 2 to FIG. 4 illustrate a state in which a twisting load due to rotation of a rotational portion 73 is not applied to the cable 100, that is, a state in which the cable 100 is not twisted. The state in which a twisting load is not applied refers to a state in which the rotational portion 73 is located at the central position within a range where the rotational portion 73 is rotatable about a rotational-shaft portion 72 described later, and in which the central axis of the cable 100 exists on a plane passing through the central axis (the third axis $O_3$) of the rotational-shaft portion 72. Specifically, the central position within the range where the rotational portion 73 is rotatable about the rotational-shaft portion 72 is a middle position between rotation limit positions of the cable 100 that rotates with the rotation of the rotational portion 73. When an angle formed between one rotation limit position and the other rotation limit position about the rotation center (the third axis $O_3$) is 300°, the central position is at an angle of 150°. If a twisting load is not applied to the cable 100, a position slightly displaced from the middle position may be defined as the central position.

The third joint portion 13 has a cylindrical shape and includes the cover 70 (see FIG. 2) whose outer circumference has the second arm portion 22 attached, an extending portion 71 that extends from an end portion of the third arm portion 23 along the longitudinal direction of the third arm portion 23 (the third axis $O_3$), the rotational-shaft portion 72 provided at an end portion of the extending portion 71, which is opposite to an end portion closer to the fourth joint portion 14, where the central axis of the rotational-shaft portion 72 corresponds with the third axis $O_3$ described above, and the rotational portion 73 rotatable about the rotational-shaft portion 72.

The extending portion 71 includes a fixed portion 711 having a disk shape fixed to the rotational-shaft portion 72, a connecting portion 712 having a plate shape connected with the fixed portion 711, while connecting the fixed portion 711 and the third arm portion 23, and a guide portion 713 having a C-shape fixed at its open end to the connecting portion 712, so as to form a hollow space through which a plurality of cables including the cable 100 are inserted and can be guided. The connecting portion 712, which has a plate shape, extends along the third axis $O_3$.

The rotational portion 73 is connected with an inner peripheral portion of the cover 70 by a connecting member 701. Thus, as the rotational portion 73 rotates about the rotational-shaft portion 72, the cover 70 also rotates in conjunction with the rotation of the rotational portion 73. As the cover 70 rotates, the second arm portion 22 rotates about the rotational-shaft portion 72 (the third axis $O_3$).

In the third joint portion 13, a plurality of cables including the cable 100 are fixed to the connecting portion 712 and the rotational portion 73 respectively by binding bands 714 and 731. Specifically, the binding band 714 is inserted through the connecting portion 712 to fix the cables including the cable 100 to the connecting portion 712. The binding band 731 surrounds the plural cables including the cable 100 and the outer periphery of the rotational portion 73 to fix the plural cables including the cable 100 to the rotational portion 73. It is preferable that the fixing position of the cable 100 by the binding bands 714 and 731 are located respectively at one end and the other end of the third joint portion 13 in the direction of the third axis $O_3$. The terms "one end" and "the other end" described herein include the end portion and a region around this end portion within a predetermined range. That is, each of the fixing positions is preferably located in a region on the side of each end portion.

The cable 100 is fixed by the binding band 714 at a position where the central axis of the cable 100 substantially corresponds with the third axis $O_3$, in the guide portion 713. The cable 100 is also fixed by the binding band 731 at a position different from the position on the third axis $O_3$, in the rotational portion 73. Thus, the fixed section of the cable 100 in the connecting portion 712 and the fixed section of the cable 100 in the rotational portion 73 are in an offset state when viewed from the direction of the third axis $O_3$. The term "offset" refers to a state in which the fixed section of the cable 100 in the connecting portion 712 and the fixed section of the cable 100 in the rotational portion 73 are located at different positions when viewed from the direction of the third axis $O_3$.

Figure 5:
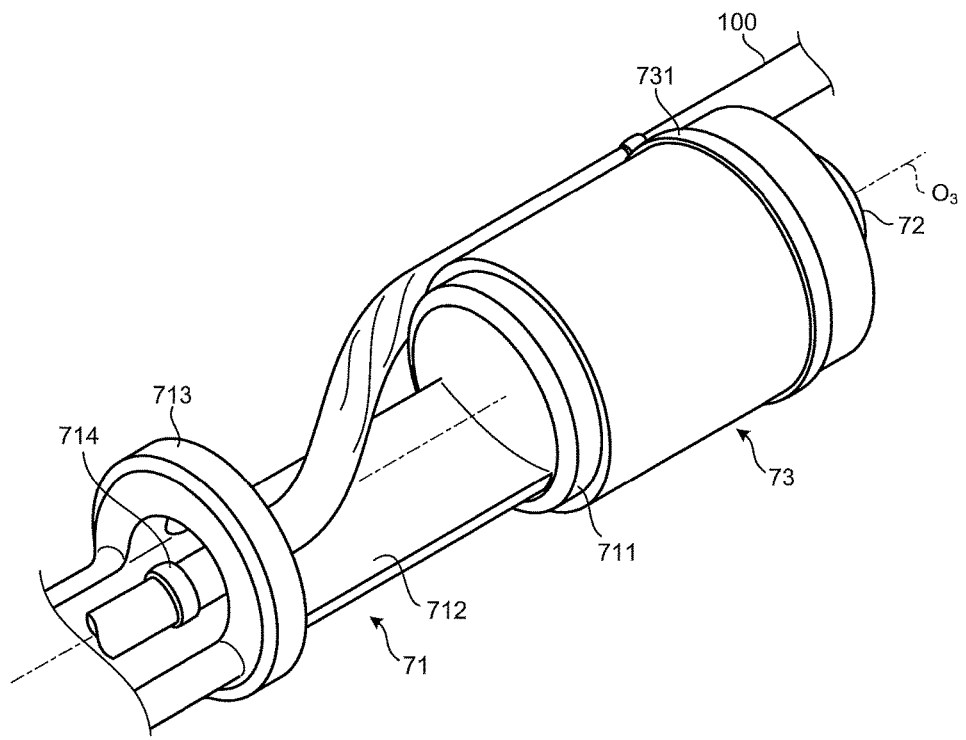
FIG. 5 is a perspective view illustrating a configuration of relevant parts of the medical observation system according to the embodiment of the present invention, for explaining a cable state when a rotational portion is rotated from a state illustrated in FIG. 4.

FIG. 5 is a perspective view illustrating a configuration of relevant parts of the medical observation system according to the embodiment of the present invention, for explaining a cable state when the rotational portion 73 is rotated from the state illustrated in FIG. 4. In the state illustrated in FIG. 5, a twisting load due to rotation of the rotational portion 73 is applied to the cable 100. At this time, in the third joint portion 13, the cable 100 is twisted in a state in which the fixed section of the cable 100 in the connecting portion 712 and the fixed section of the cable 100 in the rotational portion 73 are offset.

A distance $D_1$ (see FIG. 3) is expressed as, for example, $\frac{1}{2} \times R_1 + \frac{1}{2} \times R_2$, where $R_1$ represents the diameter of the cable 100, $R_2$ represents the outer peripheral diameter of the rotational portion 73, and $D_1$ represents the distance between the third axis $O_3$ and the center of the cable 100. The diameter $R_1$ and the distance $D_1$ preferably satisfy a relation $2 \times R_1 \leq D_1$. The third axis $O_3$ passes through the fixed section of the cable 100 in the extending portion 71, while the fixed section of the cable 100 in the rotational portion 73 is offset from the third axis $O_3$. Thus, a twisting load applied to the cable 100 due to the rotation of the rotational portion 73 is reduced as compared to a twisting load to be applied to the cable 100 in a state in which the central axis of the cable 100 corresponds with the third axis $O_3$. In a case with the cable group into which plural cables are bundled, the center of the cable 100 is replaced with the gravity center of a shape formed by the outer periphery of the cable group.

Additionally, the diameter $R_2$ and a width $D_3$ (see FIG. 4) preferably satisfy a relation $D_3 < R_2$, where $D_3$ represents the width of the connecting portion 712 that is the width on the main surface in a direction perpendicular to the third axis $O_3$. The term "main surface" described herein refers to a surface occupying the largest area of the connecting portion 712. When this relation is satisfied, it is effective in view of reducing interference between the cable 100 and the connecting portion 712 when the rotational portion 73 is rotated. As the width $D_3$ is increased while satisfying the above relation, the connection of the rotational-shaft portion 72 and the third arm portion 23 can become more rigid.

Moreover, a greater distance $D_2$ is preferable from a viewpoint of reduction in twisting load, where $D_2$ represents the distance from an end portion of the extending portion 71 on the side of the rotational portion 73 to the fixed end of the cable 100 by the binding band 714, that is the fixed end on the side of the rotational portion 73 (see FIG. 3).

As illustrated in FIG. 5, when the rotational portion 73 is rotated, the cable 100 is wound around the connecting portion 712. As the cable 100 is wound around the connecting portion 712, twisting of the cable 100 about its own central axis can be suppressed. This also applies to a case where the rotational portion 73 is rotated in a reverse direction from the central position.

According to the above embodiment, the third joint portion 13 includes the rotational-shaft portion 72 that extends in parallel to the central axis of the second arm portion 22 that is a rotation target, the rotational portion 73 that holds the second arm portion 22, fixes the cable 100 at a position offset from the central axis of the rotational-shaft portion 72, and is rotatable about the central axis of the rotational-shaft portion 72, and the extending portion 71 that extends from the rotational-shaft portion 72 and fixes the cable 100 at a position at which the central axis of the rotational-shaft portion 72 passes through the cable 100. With this, when the rotational portion 73 is rotated, the cable 100 is wound around the extending portion 71, and thus twisting of the cable 100 is suppressed. As a result, the observation apparatus 2 can be provided with durability against rotation of the arm. Further, because the arm portion is rotated (twisted), with durability being provided, the flexibility in locating the microscope unit 6 relative to the observation target can be improved.

Furthermore, according to the above embodiment, a twisting load to be applied to the cable 100 due to the rotation of the rotational portion 73 is reduced as compared to a twisting load to be applied to the cable 100 in a state in which the central axis of the cable 100 corresponds with the third axis $O_3$. Thus, when the observation apparatus 2 is used, an operational force at the time of performing operation so as to twist the arm portion about this axis (the third axis $O_3$) can be reduced.

First Modification of the Embodiment

In the above embodiment, in the extending portion 71, the connecting portion 712 is described as extending in an identical cross-sectional shape from one end portion on the side continuous to the guide portion 713 to the other end portion on the side continuous to the fixed portion 711. However, as long as the connecting portion 712 has such a shape as not to interfere with the movable path of the cable 100, for example, when the cable 100 is wound around the connecting portion 712 in a twisted state as illustrated in FIG. 5, the same effects as those obtained in the above embodiment can also be achieved even when, for example, the connecting portion 712 is shaped so as to increase its cross-sectional area near the fixed portion 711 to improve the rigidity.

Figure 6:
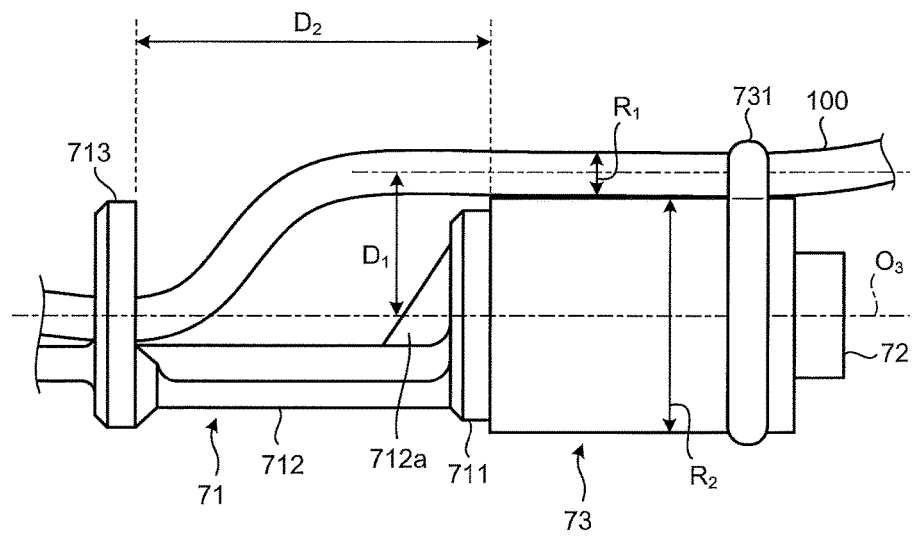
FIG. 6 is a side view illustrating a configuration of relevant parts of a medical observation system according to a first modification of the embodiment of the present invention.
Figure 7:
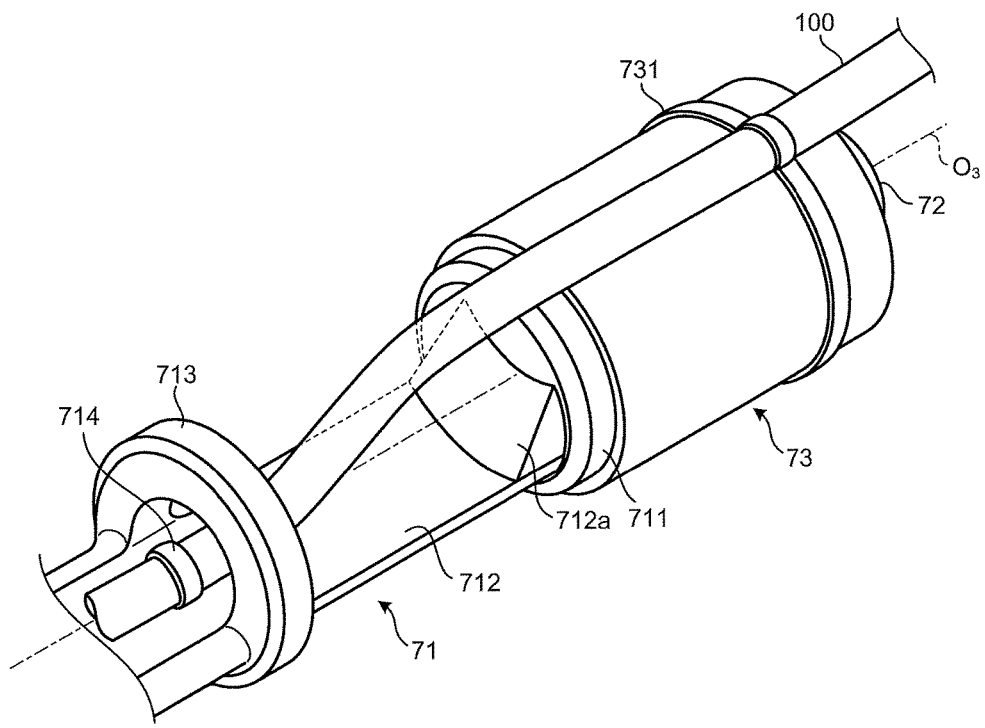
FIG. 7 is a perspective view illustrating a configuration of relevant parts of the medical observation system according the first modification of the embodiment of the present invention.
Figure 8:
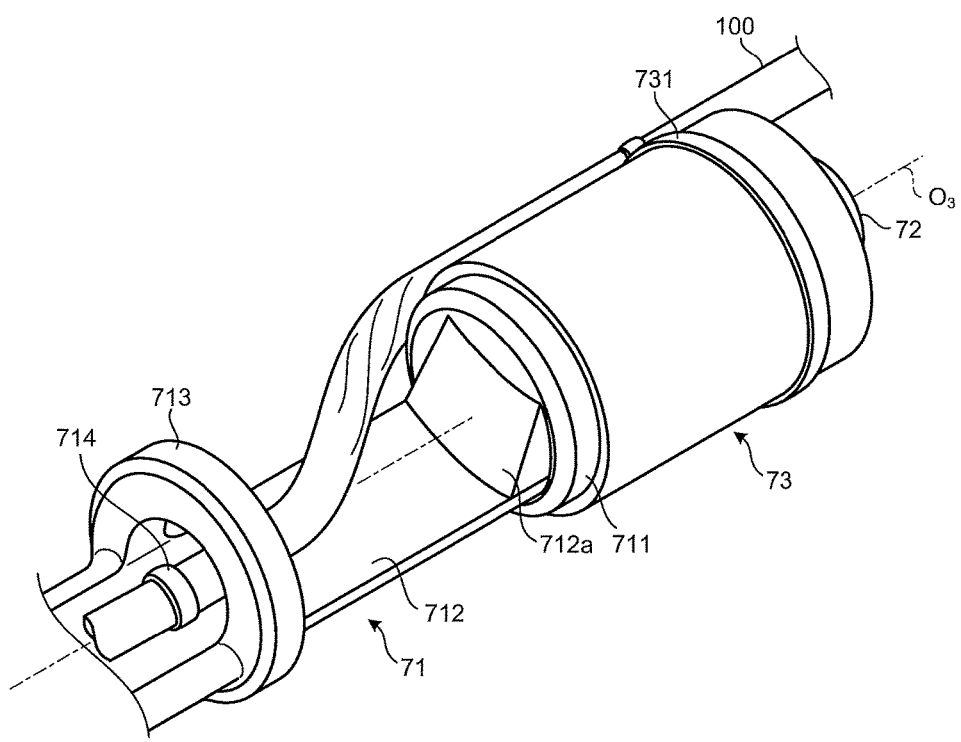
FIG. 8 is a perspective view illustrating a configuration of relevant parts of the medical observation system according the first modification of the embodiment of the present invention, for explaining a cable state when a rotational portion is rotated from a state illustrated in FIG. 7.

FIG. 6 is a side view illustrating a configuration of relevant parts of a medical observation system according to a first modification of the embodiment of the present invention. FIG. 7 is a perspective view illustrating a configuration of relevant parts of the medical observation system according to the first modification of the embodiment of the present invention. FIG. 8 is a perspective view illustrating a configuration of relevant parts of the medical observation system according to the first modification of the embodiment of the present invention, for explaining a cable state when the rotational portion is rotated from the state illustrated in FIG. 7.

In the first modification of the present embodiment, the connecting portion 712 is provided with a solid reinforcement portion 712a that includes an inclined surface inclined with respect to the third axis $O_3$, at an end portion on the side continuous to the fixed portion 711 in the direction of the third axis $O_3$. By this reinforcement portion 712a, the cross-sectional area of the connecting portion 712 is increased near the fixed portion 711, and thus can improve the rigidity of the portion around the fixed portion 711.

Second Modification of Embodiment

In the above embodiment, the cable 100 is described as a cable positioned on the outermost periphery of the cable group. However, it is also possible that a plurality of cables, such as a light guide cable and a transmission cable, are combined into a single cable.

Figure 9:
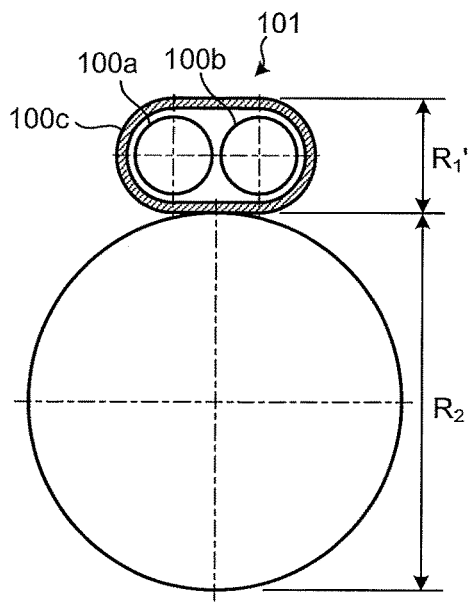
FIG. 9 is a partial cross-sectional diagram for explaining a configuration of relevant parts of a medical observation system according to a second modification of the embodiment of the present invention, illustrating a cross section passing through a rotational portion and being perpendicular to a third axis.

FIG. 9 is a partial cross-sectional diagram for explaining a configuration of relevant parts of the medical observation system according to a second modification of the embodiment of the present invention, illustrating a cross section passing through the rotational portion 73 and being perpendicular to the third axis $O_3$.

The second modification of the present embodiment is described as using a combined cable 101 in which two cables (a first cable 100a and a second cable 100b) are aligned in their extending directions and combined into one by a covering material 100c. In this case, a length $R_1'$ equivalent to the diameter $R_1$ of the cable 100 is a minimum length between the outermost surfaces of the covering material 100c in a direction perpendicular to the third axis $O_3$ (see FIG. 3 and other diagrams). The length $R_1'$ and the distance $D_1$ preferably satisfy a relation $2 \times R_1' \leq D_1$ as described in the above embodiment.

Third Modification of Embodiment

Figure 10:
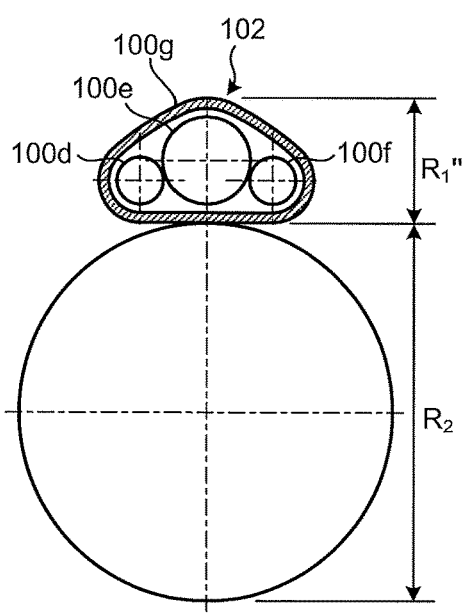
FIG. 10 is a partial cross-sectional diagram for explaining a configuration of relevant parts of a medical observation system according to a third modification of the embodiment of the present invention, illustrating a cross section passing through a rotational portion and being perpendicular to a third axis.

FIG. 10 is a partial cross-sectional diagram for explaining a configuration of relevant parts of a medical observation system according to a third modification of the embodiment of the present invention, illustrating a cross section passing through the rotational portion 73 and being perpendicular to the third axis $O_3$.

The third modification of the present embodiment is described as using a combined cable 102 in which three cables (a first cable 100d, a second cable 100e, and a third cable 100f) are aligned in their extending directions and combined into one by a covering material 100g. In this case, a length $R_1''$ equivalent to the diameter $R_1$ of the cable 100 is a minimum length between the outermost surfaces of the covering material 100g in a direction perpendicular to the third axis $O_3$ (see FIG. 3 and other diagrams). The length $R_1''$ and the distance $D_1$ preferably satisfy a relation $2 \times R_1'' \leq D_1$ as described in the above embodiment.

In the combined cables 101 and 102 used respectively in the above second and third modifications, in a state in which the rotational portion 73 and the extending portion 71 are not twisted, at least one of the cables exists on a plane passing through the central axis of the rotational-shaft portion 72, that is on a plane passing through a substantially central position within a rotatable range.

While the embodiment of the present invention has been described above, the present invention is not limited only to the above embodiment. In the above embodiment, the configuration of the third joint portion 13 is described as an example. However, such configuration is also applicable to a joint portion (a twisting portion) that rotates a rotation-target member about an axis parallel to the central axis of the rotation-target member. Specifically, when the configuration is applied to the first joint portion 11, the sixth joint portion 16, and the like, the effects described above can also be obtained.

In the above-described embodiment, the cable 100 is described as being fixed to the connecting portion 712 and the rotational portion 73 respectively by the binding bands 714 and 731. However, a cable fixing member is not limited to the binding band as long as the cable 100 can be fixed to each of the connecting portion 712 and the rotational portion 73.

In the above-described embodiment, the observation apparatus 2 is described as including the cable group including a transmission cable through which a signal is transmitted, and a light guide cable through which illumination light is guided. In a case where the observation apparatus 2 does not include a light guide cable because of using an external light source device or the like, the observation apparatus 2 may include a single cable, e.g., one having only a transmission cable, or the like.

INDUSTRIAL APPLICABILITY

As described above, the medical observation apparatus and the medical observation system according to the present invention is useful in providing durability against rotation of an arm.

REFERENCE SIGNS LIST 1 medical observation system
2 medical observation apparatus
3 display device
4 base unit 5 support unit
6 microscope unit
11 first joint portion
12 second joint portion
13 third joint portion
14 fourth joint portion
15 fifth joint portion
16 sixth joint portion
21 first arm portion
22 second arm portion
23 third arm portion
24 fourth arm portion
25 fifth arm portion
70 cover
71 extending portion
72 rotational-shaft portion
73 rotational portion
100 cable
101, 102 combined cable
711 fixed portion
712 connecting portion
713 guide portion
714, 731 binding band

The invention claimed is:

1. A medical observation apparatus comprising:
a microscope unit that outputs a signal of a captured image of an observation target;
a support unit that movably supports the microscope unit and that includes a plurality of arm portions and a plurality of joint portions, each of which holds the arm portions rotatably about a predetermined axis; and
one or a plurality of cables connected to the microscope unit and inserted through an interior of the support unit, wherein
at least one of the joint portions includes a twisting joint portion that rotates a rotation-target arm portion about an axis parallel to a central axis of the rotation-target arm portion, and
the twisting joint portion includes
a rotational-shaft portion that extends in parallel to the central axis of the rotation-target arm portion,
a rotational portion that holds the rotation-target arm portion, fixes the cable at a position offset from a central axis of the rotational-shaft portion, and is rotatable about the central axis, and
an extending portion that extends from the rotational-shaft portion and fixes the cable at a position where the central axis of the rotational-shaft portion passes through the cable.

2. The medical observation apparatus according to claim 1, wherein
the extending portion includes
a fixed portion fixed to the rotational-shaft portion, and
a connecting portion having a plate shape that fixes the cable thereto and is connected with the fixed portion.

3. The medical observation apparatus according to claim 2, wherein
the rotational portion has a cylindrical shape and is located on an outer peripheral side of the rotational-shaft portion, and
a plate width of the connecting portion on a main surface is smaller than an outer peripheral diameter of the rotational portion.

4. The medical observation apparatus according to claim 3, wherein a relation $2 \times R_1 \leq D_1$ is satisfied, where R1 represents a diameter of the cable, and $D_1$ represents a distance between the central axis of the rotational-shaft portion and a center of the cable.

5. The medical observation apparatus according to claim 1, wherein a fixing position of the cable in the rotational portion, and a fixing position of the cable in the extending portion are located respectively at one end and the other end of the twisting joint portion in a direction of the central axis of the rotational-shaft portion.

6. The medical observation apparatus according to claim 1, wherein at least one of the cables exists on a plane passing through the central axis of the rotational-shaft portion in a state in which the rotational portion and the extending portion are not twisted.

7. The medical observation apparatus according to claim 6, wherein in a state in which the rotational portion and the extending portion are not twisted, a plane passing through at least one of the cables and passing through the central axis of the rotational-shaft portion is a plane passing through substantially a center within a range where the cable is rotatable when the rotational portion rotates about the central axis.

8. A medical observation system comprising:
the medical observation apparatus according to claim 1; and
a display device that displays an image corresponding to image data generated by the medical observation apparatus.

9. A medical observation apparatus comprising:
a microscope that outputs a signal of a captured image of an observation target;
a support arm that movably supports the microscope and that includes a plurality of arms and a plurality of joints, each of which holds the plurality of arms rotatably about a predetermined axis; and
one or a plurality of cables connected to the microscope and inserted through an interior of the support arm, wherein
at least one of the joints includes a twisting joint that rotates a rotation-target arm about an axis parallel to a central axis of the rotation-target arm, and
the twisting joint includes
a rotational-shaft that extends in parallel to the central axis of the rotation-target arm,
a rotational holder that holds the rotation-target arm, fixes the cable at a position offset from a central axis of the rotational-shaft, and is rotatable about the central axis, and
an extending shaft that extends from the rotational-shaft and fixes the cable at a position where the central axis of the rotational-shaft passes through the cable.

10. The medical observation apparatus according to claim 9, wherein
the extending shaft includes
a fixed disk fixed to the rotational-shaft, and
a connector having a plate shape that fixes the cable thereto and is connected to the fixed disk.

11. The medical observation apparatus according to claim 10, wherein
the rotational holder is located on an outer peripheral side of the rotational-shaft, and
a plate width of the connector on a main surface is smaller than an outer peripheral diameter of the rotational holder.

12. The medical observation apparatus according to claim 11, wherein a relation $2 \times R_1 \leq D_1$ is satisfied, where R1 represents a diameter of the cable, and $D_1$ represents a distance between the central axis of the rotational-shaft and a center of the cable.

13. The medical observation apparatus according to claim 9, wherein a fixing position of the cable in the rotational holder, and a fixing position of the cable in the extending shaft are located respectively at one end and the other end of the twisting joint in a direction of the central axis of the rotational-shaft.

14. The medical observation apparatus according to claim 9, wherein at least one of the cables exists on a plane passing through the central axis of the rotational-shaft in a state in which the rotational holder and the extending shaft are not twisted.

15. The medical observation apparatus according to claim 14, wherein in a state in which the rotational holder and the extending shaft are not twisted, a plane passing through at least one of the cables and passing through the central axis of the rotational-shaft is a plane passing through substantially a center within a range where the cable is rotatable when the rotational holder rotates about the central axis.

16. A medical observation system comprising:
the medical observation apparatus according to claim 9; and
a display device that displays an image corresponding to image data generated by the medical observation apparatus.

17. A medical apparatus comprising:
a support arm that movably supports a medical device and that includes a plurality of arms and a plurality of joints, each of which holds the arms rotatably about a predetermined axis; and
one or a plurality of cables connected to the medical device and inserted through an interior of the support arm, wherein
at least one of the joints includes a twisting joint that rotates a rotation-target arm about an axis parallel to a central axis of the rotation-target arm, and
the twisting joint includes
a rotational-shaft that extends in parallel to the central axis of the rotation-target arm,
a rotational holder that holds the rotation-target arm, fixes the cable at a position offset from a central axis of the rotational-shaft, and is rotatable about the central axis, and
an extending shaft that extends from the rotational-shaft and fixes the cable at a nearer position to the central axis than the fixed position of the cable on the rotational holder.

18. The medical apparatus according to claim 17, wherein the extending shaft includes
a fixed disk fixed to the rotational-shaft, and
a connector having a plate shape that fixes the cable thereto and is connected to the fixed disk.

19. The medical apparatus according to claim 18, wherein the rotational holder is located on an outer peripheral side of the rotational-shaft, and
a plate width of the connector on a main surface is smaller than an outer peripheral diameter of the rotational holder.

20. The medical apparatus according to claim 17, wherein a fixing position of the cable in the rotational holder, and a fixing position of the cable in the extending shaft are located respectively at one end and the other end of the twisting joint in a direction of the central axis of the rotational-shaft.

* * * * *